US00PP30846P2

(12) United States Plant Patent
Mazzardis

(10) Patent No.: US PP30,846 P2
(45) Date of Patent: Aug. 27, 2019

(54) BLUEBERRY PLANT, 'NS 14-5'

(50) Latin Name: ***Ericaceae Vaccinium* hybrid**
Varietal Denomination: NS 14-5

(71) Applicant: Vincent David Mazzardis, Joondalup (AU)

(72) Inventor: Vincent David Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 15/932,411

(22) Filed: Feb. 27, 2018

(30) Foreign Application Priority Data

Jan. 23, 2018 (ZA) ..... PBR PT 8461

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Randall Danskin P.S.

(57) ABSTRACT

A new and distinct variety of blueberry plant, which is denominated varietally as 'NS 14-5' is described, and which produces a fruit having a very large fruit size, a high fruit sweetness, a medium firmness fruit, a high fruit acidity, and displaying a small dry picking scar with a calyx depicting a strong star shape, and a high yield, when grown under the ecological conditions prevailing near Yanchep Springs, Yanchep, Western Australia.

6 Drawing Sheets

Latin name: '*Ericaceae Vaccinium* Hybrid'.
Varietal denomination: 'NS 14-5'.

BACKGROUND OF THE NEW VARIETY

The present invention relates to a new, novel, and distinct variety of blueberry plant '*Vaccinium* Hybrid' and which has been denominated varietally as 'NS 14-5'.

ORIGIN AND ASEXUAL REPRODUCTION OF THE NEW VARIETY

The present, new variety of blueberry plant resulted from an ongoing development program of plant breeding. The purpose of this program was to improve the commercial quality of various plant varieties by creating, and releasing, promising selections of plants, including blueberries. To this end, I have made both controlled, and hybrid cross-pollinations each year to produce resulting plant populations from which improved progenies are evaluated and selected.

The blueberry plant 'NS 14-5' was derived from a controlled cross-pollination, employing the blueberry plant '7-26' (unpatented), which is the seed parent, and blueberry plant 'EB 8-30' (U.S. Plant Pat. No. 25,889), which is the pollen parent, during the 2012 growing season. This first cross-pollination took place at my property, which is located at Yanchep Springs, Yanchep, Western Australia. The seed parent '7-26' is characterized, at least in part, by a semi-upright growth habit, a medium vigor, an early season ripening date, and further produces large sized, medium firmness, high sweetness, and low acidity fruit. The pollen parent 'EB 8-30', on the other hand, is characterized, at least in part, by a semi-upright growth habit and a medium vigor, and further produces medium sized, firm, high sweetness, and low acidity fruit. The seed derived as a result of the first cross-pollination from the seed parent, blueberry plant '7-26', produced approximately 600 plants. These new plants were then grown at my aforementioned property, and the first fruit was evaluated during the 2014 growing season. Further, an additional assessment of these same new plants, which took place in 2015, resulted in the new variety 'NS 14-5' being selected for further asexual reproduction and evaluation. The present, new variety showed desirable traits suitable for a commercial blueberry variety. The present, new variety was asexually reproduced by cuttings, and the plants produced from this first asexual propagation were again evaluated during the 2016 and 2017 growing seasons. The asexually reproduced plants, which were produced from the aforementioned asexual reproduction process, were subsequently evaluated, and were found to be true to the original plant. It was my conclusion, at that time, that the variety 'NS 14-5', was a new, novel, and distinct variety of blueberry plant.

In relative comparison to the closest known variety, that being the 'EB 8-46' blueberry plant (U.S. Plant Pat. No. 26,173), the new variety of blueberry plant is clearly distinguishable. The present, new variety is distinguishable from the 'EB 8-46' blueberry plant in view of its bush, which expresses a medium vigor when compared to the bush of the 'EB 8-46' blueberry plant, which expresses a medium to strong vigor. Further, the present, new variety is distinguishable from the 'EB 8-46' blueberry plant in view of the fruit it produces, which possesses a medium fruit firmness when compared to the fruit produced by the 'EB 8-46' blueberry plant, which produces very firm fruit. Still further, the present, new variety is distinguishable from the 'EB 8-46' blueberry plant (the closest known variety) in view of the fruit it produces, which possesses a high acidity when compared to the fruit produced by the 'EB 8-46' blueberry plant, which produces fruit having a low acidity. Yet further, the present, new variety is distinguishable from the 'EB 8-46' blueberry plant in view of its bush, which produces flowers and fruit on the one-year-old shoots only when compared to the bush of the 'EB 8-46' blueberry plant which produces flowers and fruit on the current year's shoots and the one-year-old shoots. Even further, the present, new variety is distinguishable from the 'EB 8-46' blueberry plant (the closest known variety) in view of its bush, which is evergreen when compared to the bush of the 'EB 8-46' blueberry plant, which is semi-evergreen.

The present, new variety is distinguishable from the '7-26' blueberry plant (the seed parent) in view of its fruit, which has a high acidity when compared to the fruit of the '7-26' blueberry plant, which produces fruit having a low acidity. Further, the present, new variety is distinguishable from the '7-26' blueberry plant in view of the fruit it produces, which possesses a very large fruit size when compared to the fruit produced by the '7-26' blueberry plant, which produces fruit having a large fruit size. Still further, the present, new variety is distinguishable from the '7-26' blueberry plant in view of its time of beginning of flowering on one-year-old shoots which is April when grown under the ecological conditions present in Yanchep Springs, Yanchep, Western Australia, when compared to the time of beginning of flowering on one-year-old shoots of the '7-26' blueberry plant, which is late June or early July when grown under the ecological conditions present near Yanchep Springs, Yanchep, Western Australia. Yet further, the present, new variety is distinguishable from the '7-26' blueberry plant (the seed parent) in view of its time of beginning of fruit ripening on one-year-old shoots which is July when grown under the ecological conditions present in Yanchep Springs, Yanchep, Western Australia, when compared to the time of beginning of fruit ripening on one-year-old shoots of the '7-26' blueberry plant, which is September when grown under the ecological conditions present in Yanchep Springs, Yanchep, Western Australia. Even further, the present, new variety is distinguishable from the '7-26' blueberry plant (the seed parent) in view of its bush, which is considered evergreen when compared to the bush of the '7-26' blueberry plant, which is considered semi-evergreen.

The present, new variety is distinguishable from the 'EB 8-30' blueberry plant (U.S. Plant Pat. No. 25,889) (the pollen parent) in view of the fruit it produces, which possesses a medium fruit firmness when compared to the fruit produced by the 'EB 8-30' blueberry plant, which produces firm fruit. Further, the present, new variety is distinguishable from the 'EB 8-30' blueberry plant in view of the fruit it produces, which possesses a high fruit acidity when compared to the fruit produced by the 'EB 8-30' blueberry plant which produces fruit having a low acidity. Still further, the present, new variety is distinguishable from the 'EB 8-30' blueberry plant (the pollen parent) in view of the fruit it produces, which possesses a very large fruit size when compared to the fruit produced by the 'EB 8-30' blueberry plant, which produces fruit having a medium to large fruit size. Yet further, the present, new variety is distinguishable from the 'EB 8-30' blueberry plant in view of its time of beginning of flowering on one-year-old shoots which is April when grown under the ecological conditions present in Yanchep Springs, Yanchep, Western Australia, when compared to the time of beginning of flowering on one-year-old shoots of the 'EB 8-30' blueberry plant, which is July when grown under the ecological conditions present near Yanchep Springs, Yanchep, Western Australia. Yet further, the present, new variety is distinguishable from the 'EB 8-30' blueberry plant (the pollen parent) in view of its bush, which produces flowers and fruit on the one-year-old shoots only when compared to the bush of the 'EB 8-30' blueberry plant, which produces flowers and fruit on the current year's shoots and the one-year-old shoots.

BRIEF DESCRIPTION OF THE DRAWINGS

The accompanying drawings which are provided are color photographs of the new blueberry plant 'NS 14-5'.

Figure 1:
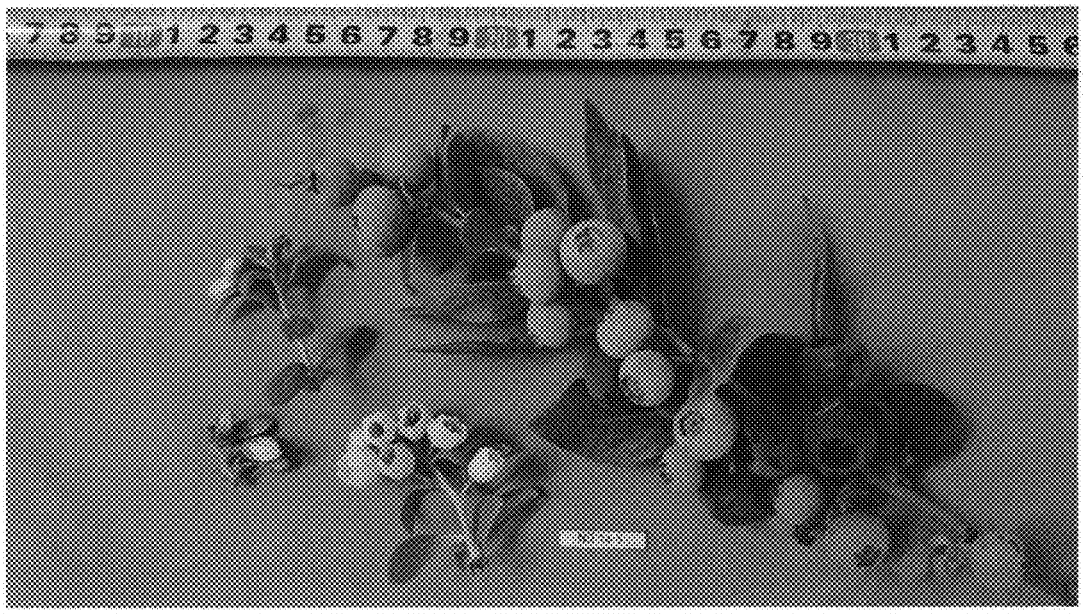
FIG. 1 is a color photograph, which shows the leaves, flowers, and fruit of the new blueberry plant 'NS 14-5'. This photograph depicts several ripe and unripe fruit, the ripe fruit being sufficiently mature for harvesting and shipment, and further shows flowers at different stages of development, and still further shows typical shoot-bearing leaves, and the ventral and dorsal colorations thereof.
Figure 2:
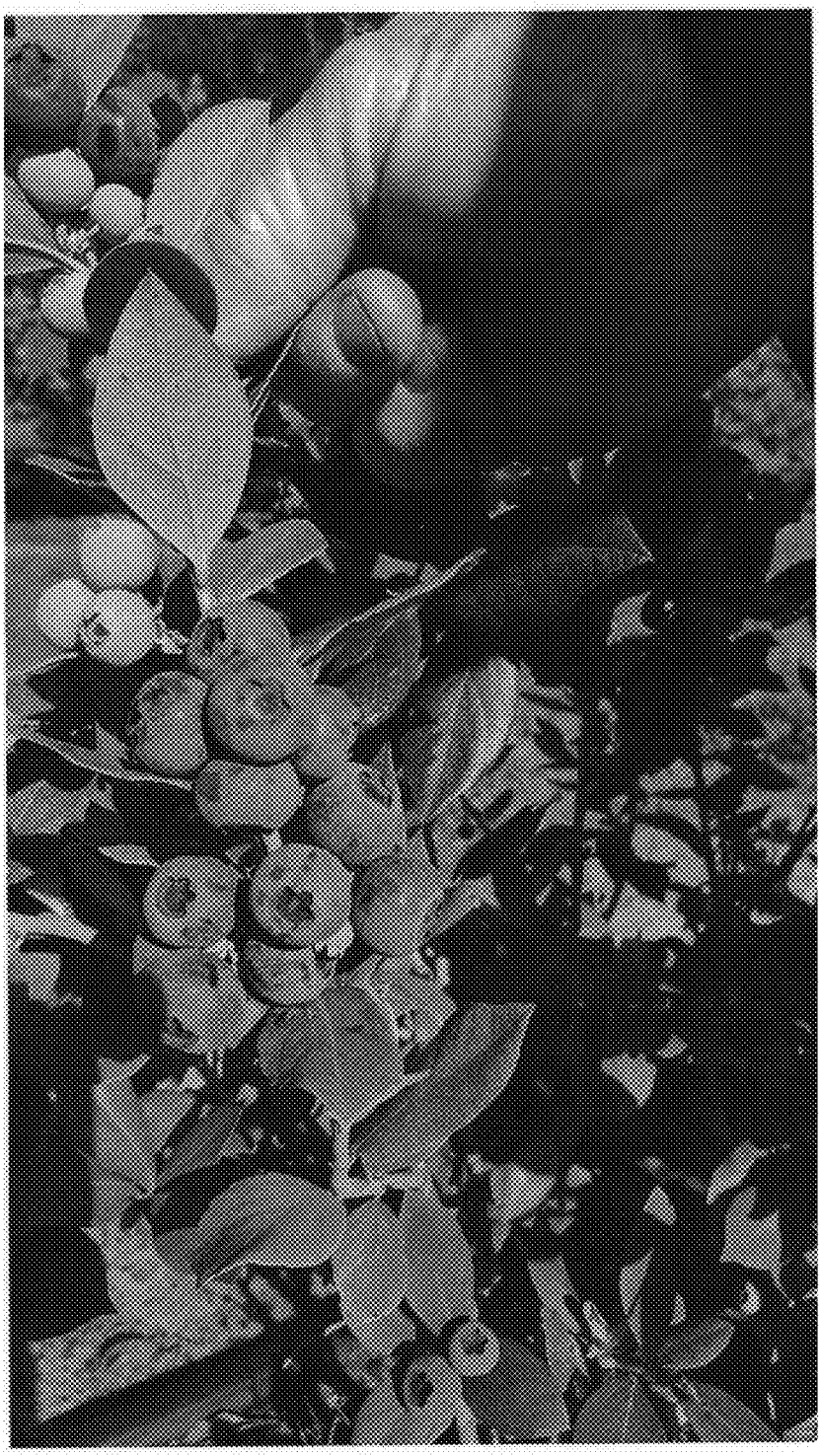
FIG. 2 is a color photograph, which shows the new blueberry plant 'NS 14-5'. This photograph depicts a mature bush with ripe and unripe fruit, the ripe fruit being sufficiently mature for harvesting and shipment, the very large fruit size, and several leaves showing the dorsal and ventral colorations thereof.
Figure 3:
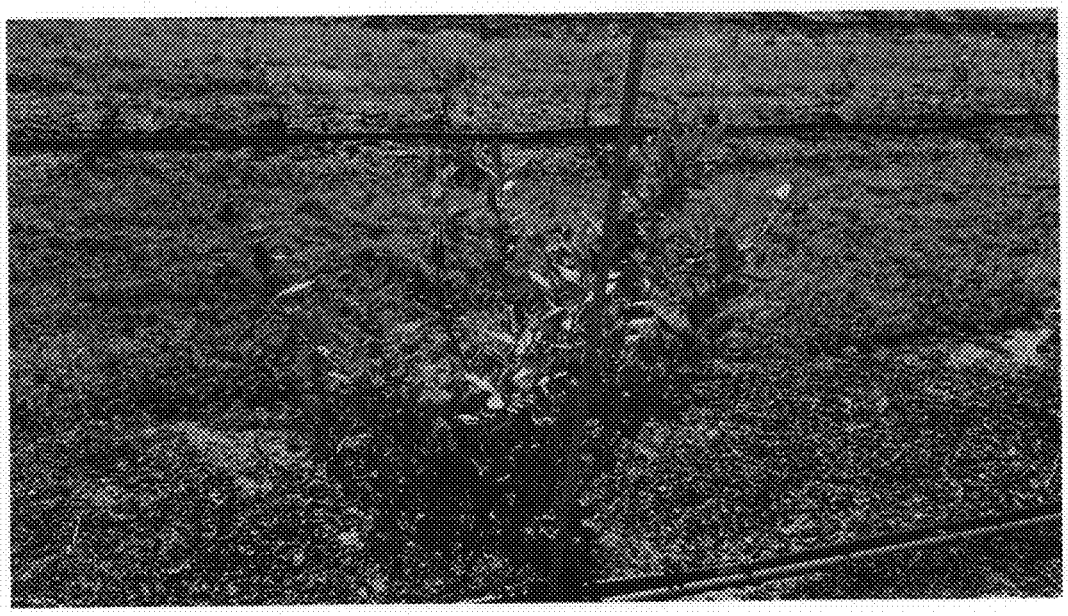
FIG. 3 is a color photograph, which shows the new blueberry plant 'NS 14-5'. This photograph depicts a mature bush with ripe and unripe fruit, the ripe fruit being sufficiently mature for harvesting and shipment and the semi-upright growth habit of the bush.
Figure 4:
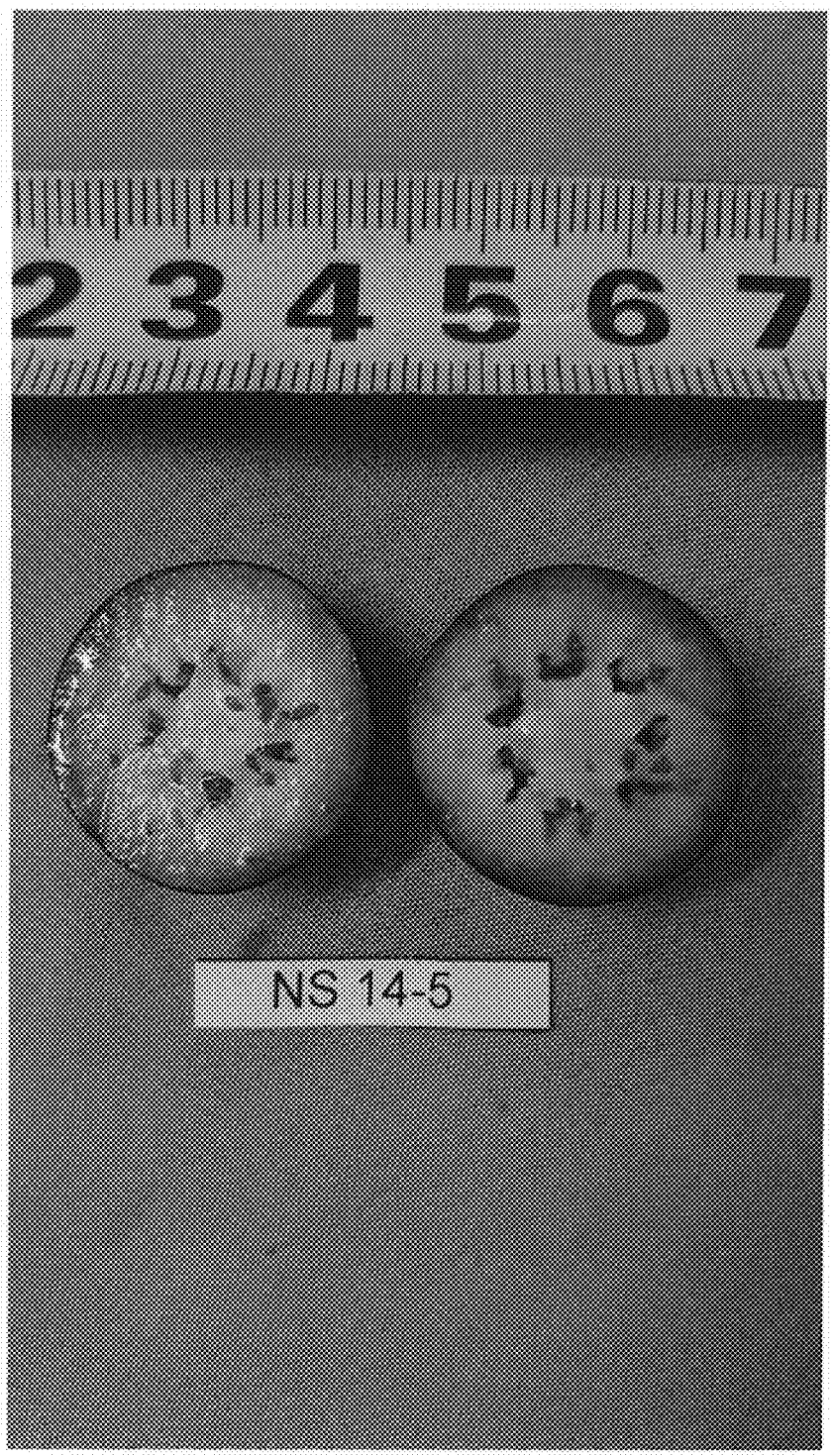
FIG. 4 is a color photograph, which shows the fruit of the new blueberry plant 'NS 14-5'. This photograph depicts a cross-sectional view of a ripe fruit, the fruit being sufficiently mature for harvesting and shipment, the very large fruit size, the color of the ripe fruit flesh (RHS Light Yellow Green 145B), and the color of the seeds (RHS Moderate Orange 167A).
Figure 5:
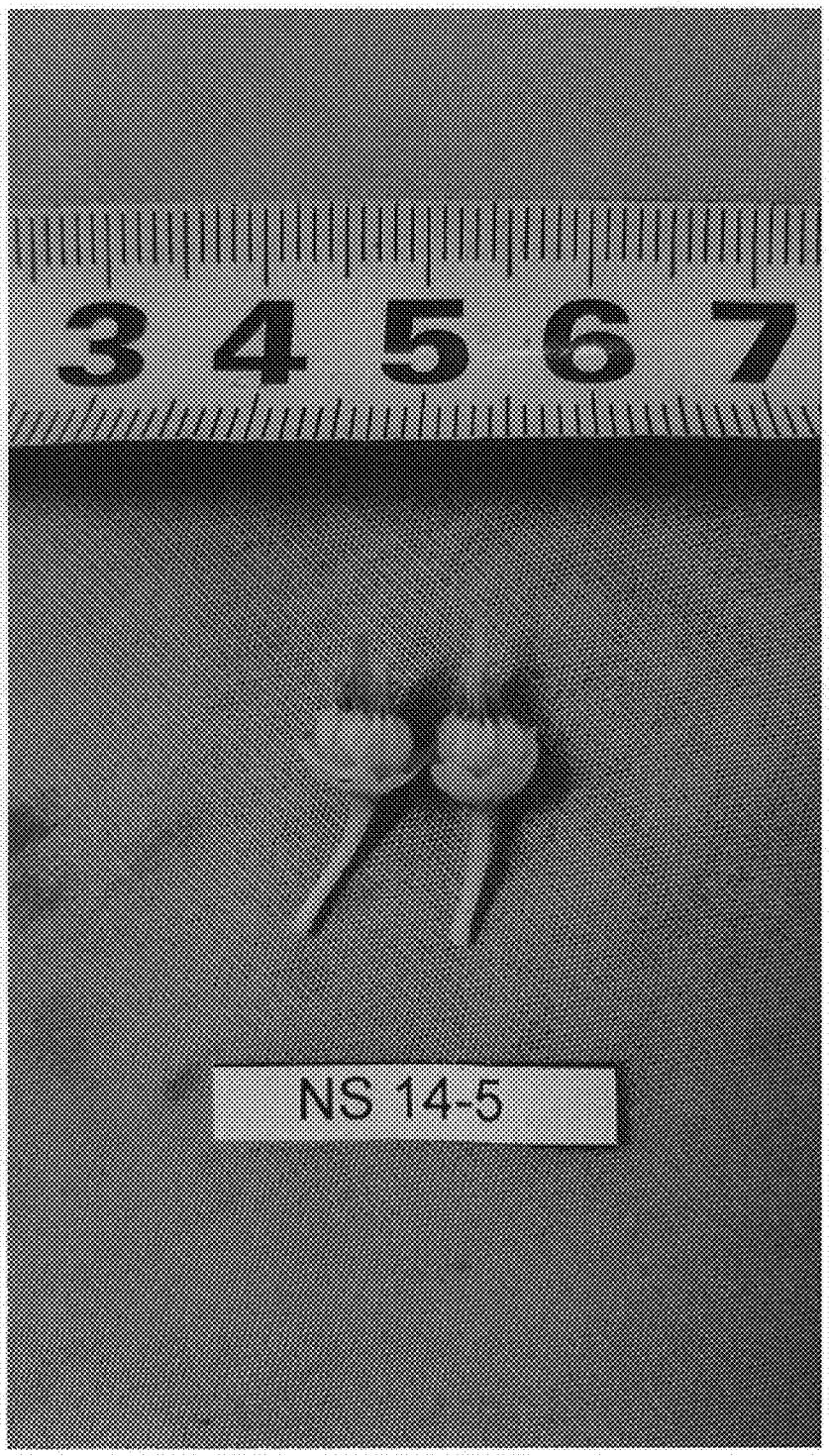
FIG. 5 is a color photograph, which shows the interior of the flowers of the new blueberry plant 'NS 14-5'. This photograph depicts flowers with the petals removed, showing the sepals, the pistil, and the filament and anthers, which comprise the stamen.
Figure 6:
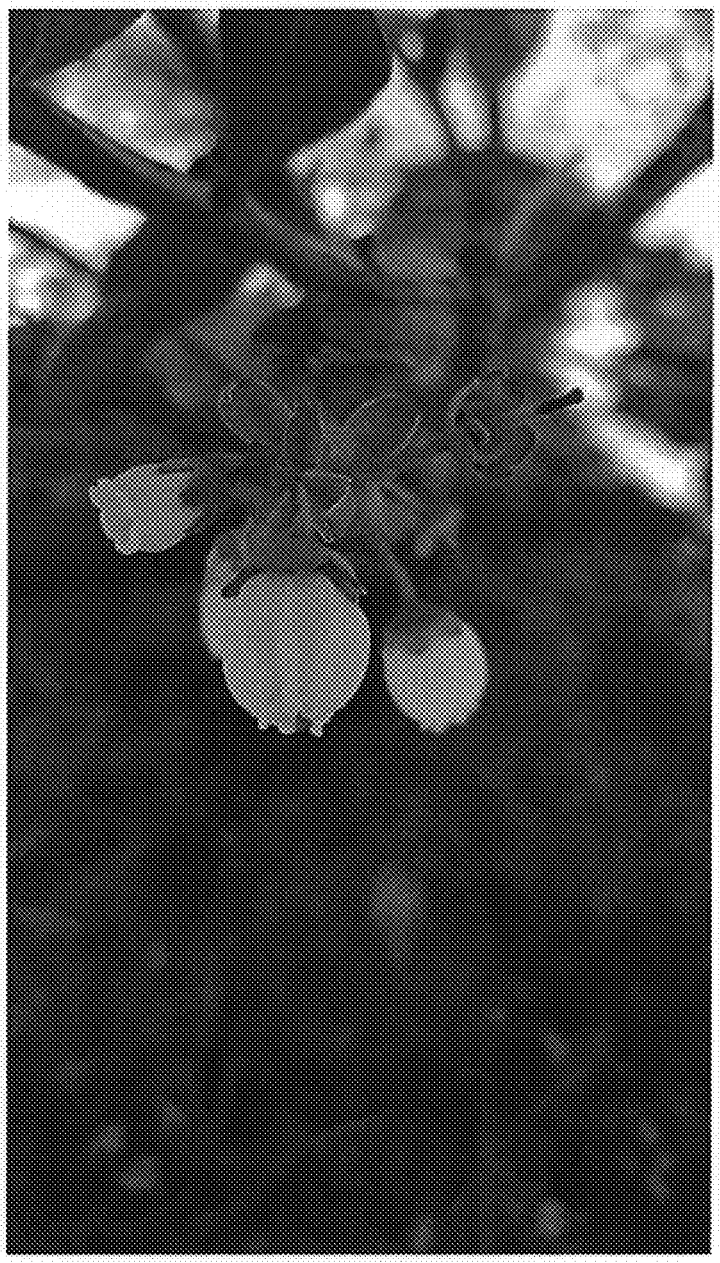
FIG. 6 is a color photograph, which shows the flowers of the new blueberry plant 'NS 14-5'. This photograph depicts a mature bush with flowers that are fully mature, including the sepals and the petals of the flowers.

The colors in the attached photographs are as nearly true as reasonably possible in a color representation of this type. Due to chemical development, processing and printing, the leaves and fruit depicted in these photographs may or may not be accurate when compared to the actual specimens. For this reason, future color references should be made to the color plates (Royal Horticultural Society $6^{th}$ Edition, hereinafter R.H.S.), and the color descriptions as provided, hereinafter.

NOT A COMMERCIAL WARRANTY

The following detailed description has been prepared solely to comply with the provisions of 35 U.S.C. § 112, and does not constitute a commercial warranty (either expressed or implied), that the present, new variety will, in the future, display the botanical, horticultural, or other characteristics as set forth, hereinafter. Therefore, this disclosure may not be relied upon to support any future legal claims including, but not limited to, breach of warranty and merchantability, or fitness for any particular purpose, or non-infringement which is directed, in whole, or in part, to the present, new variety.

DETAILED DESCRIPTION

Referring more specifically to the botanical details of this new and distinct variety of blueberry plant, the following has been observed during the 2016 growing season under the ecological conditions prevailing at the farm of the inventor, and which is located near Yanchep Springs, Yanchep, Western Australia.

Plant:

*Plant vigor.*—Considered to be medium for the variety.

*Plant growth habit.*—Considered to be semi-upright.

*Size of plant.*—On average, about 1.2 meters by 1.0 meters.

*Internode length.*—One-Year-Old Shoots: On average, about 12.0 to 18.0 mm. This is considered to be medium for the variety.

*Color, one-year-old shoots.*—Medium Yellow Green (RHS 139D).

*Fruiting type.*—One-year-old shoots only.

Leaves:

*Leaf length.*—On average, about 70.4 mm. This is considered to be a very long length for the variety.

*Leaf width.*—On average, about 32.8 mm. This is considered to be a broad width for the variety.

*Leaf ratio, length/width.*—On average, about 2.15.

*Color of leaf, dorsal surface.*—Medium Yellow Green (RHS 138B).

*Color of leaf, ventral surface.*—Medium Yellow Green (RHS 137C).

*Color of leaf, vein.*—Strong Yellow Green (RHS N144D).

*Venation pattern of leaf.*—Reticulate pinnate.

*Leaf apex texture.*—Glabrous.

*Leaf apex shape.*—Acuminate.

*Leaf base shape.*—Cuneate.

*Leaf shape.*—Elliptic.

*Leaf marginal edge.*—Entire.

*Leaf arrangement of plant.*—Alternate.

*Vegetative bud burst, date.*—February, when grown under the ecological conditions prevailing near Yanchep Springs, Yanchep, Western Australia. The present, new variety is considered to be evergreen.

Flowers:

*Inflorescence length, excluding peduncle.*—Considered to be medium for the variety.

*Flower bud, coloration.*—The presence of anthocyanin is considered to be strong in the flower buds for the variety; color White (RHS NN155C).

*Beginning of flowering on one-year-old shoots.*—April when grown under the ecological conditions prevailing near Yanchep Springs, Yanchep, Western Australia.

*Beginning of flowering on current year's shoots.*—Flowering does not occur on current year's shoots.

*Corolla shape.*—Urceolate.

*Corolla ridges.*—Present.

*Corolla tube size.*—10.0 by 10.0 mm. This is considered to be medium to large for the variety.

*Corolla tube, coloration.*—The presence of anthocyanin is considered to be absent to very weak on the corolla tube.

*Calyx diameter.*—On average, about 8.0 mm. This is considered to be large for the variety.

*Calyx basin depth.*—Considered to be deep for the variety.

*Attitude of sepals.*—Considered to be erect.

*Type of sepals.*—Considered to be straight.

Reproductive organs:

*Pollination requirements.*—The variety is self-fertile.

*Pistil length.*—On average, about 8.59 mm.

*Pistil color.*—Light Yellow Green (RHS 145B).

Fruit:

*Unripe fruit, intensity of green color.*—Considered to be light for the variety.

*Ripe fruit skin, color.*—Bluish Black (RHS 203D).

*Ripe fruit, size.*—On average, about 21.44 mm. This is considered to be very large for the variety.

*Berry shape, longitudinal section.*—Oblate.

*Sweetness, when ripe.*—Considered to be high for the variety.

*Firmness, when ripe.*—Considered to be medium for the variety.

*Acidity, when ripe.*—Considered to be high for the variety.

*Cluster density.*—Considered to be medium for the variety.

*Storability of the fruit.*—Considered to be excellent for the variety.

*Market use.*—Considered First Grade fresh market fruit.

*Beginning of fruit ripening on one-year-old shoots.*—July, when grown under the ecological conditions prevailing near Yanchep Springs, Yanchep, Western Australia.

*Beginning of fruit ripening on current year's shoots.*—Generally, there is no ripening on the current year's shoots.

*Harvesting date.*—October, when grown under the ecological conditions prevailing near Yanchep Springs, Yanchep, Western Australia.

*Resistance to insects and diseases.*—No particular susceptibilities were noted. The present, new variety has not been tested to expose or detect any susceptibilities or resistances to any known plant and/or fruit diseases.

Although the new variety of blueberry plant possesses the described characteristics when grown under the ecological conditions prevailing near Yanchep Springs, Yanchep, Western Australia, it should be understood that the usual variations of the magnitude and characteristics incident to changes in growing conditions, fertilization, pruning, pest control, frost, climatic variables and horticultural management are to be expected.

Having thus described and illustrated my new blueberry plant, what I claim is new, and desire to secure by plant Letters Patent is:

1. A new and distinct variety of blueberry plant, substantially as illustrated and described, and which is characterized principally as to novelty by producing a fruit having a very large fruit size, a high fruit sweetness, a medium firmness fruit, a high fruit acidity, and displaying a small dry picking scar with a calyx depicting a strong star shape, and a high yield, when grown under the ecological conditions prevailing near Yanchep Springs, Yanchep, Western Australia.

* * * * *